(12) United States Patent
Rifkin et al.

(10) Patent No.: US 10,201,498 B2
(45) Date of Patent: **\*Feb. 12, 2019**

(54) SHELF-STABLE FOAM-LIKE CONFECTIONARIES COMPRISING ERYTHRITOL AND ACTIVE INGREDIENTS

(71) Applicant: Eclaire Farm, LLC, Vancouver, WA (US)

(72) Inventors: Martin Rifkin, Vancouver, WA (US); Charles Bedell, Vancouver, WA (US)

(73) Assignee: MYBITE VITAMINS, LLC, Vancouver, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/421,694

(22) Filed: Feb. 1, 2017

(65) Prior Publication Data

US 2017/0258913 A1    Sep. 14, 2017

Related U.S. Application Data

(63) Continuation-in-part of application No. 15/141,055, filed on Apr. 28, 2016, now abandoned, which is a continuation-in-part of application No. 15/068,544, filed on Mar. 12, 2016, now abandoned.

(51) Int. Cl.

| | |
|---|---|
| *A23G 3/52* | (2006.01) |
| *A61K 9/12* | (2006.01) |
| *A23G 3/54* | (2006.01) |
| *A23G 3/42* | (2006.01) |
| *A23G 3/36* | (2006.01) |
| *A61K 47/26* | (2006.01) |
| *A61K 47/46* | (2006.01) |
| *A61K 47/42* | (2017.01) |
| *A61K 31/375* | (2006.01) |
| *A23G 3/34* | (2006.01) |
| *A23G 3/44* | (2006.01) |
| *A61K 9/00* | (2006.01) |

(52) U.S. Cl.
CPC .............. *A61K 9/122* (2013.01); *A23G 3/346* (2013.01); *A23G 3/368* (2013.01); *A23G 3/42* (2013.01); *A23G 3/44* (2013.01); *A23G 3/52* (2013.01); *A23G 3/54* (2013.01); *A61K 9/0056* (2013.01); *A61K 31/375* (2013.01); *A61K 47/26* (2013.01); *A61K 47/42* (2013.01); *A61K 47/46* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,376,003 B1 | 4/2002 | Cross | |
| 6,432,460 B1 | 8/2002 | Zietiow et al. | |
| 2004/0228951 A1 | 11/2004 | Schmidt | |
| 2005/0013923 A1* | 1/2005 | Shimek | A23G 3/36 426/660 |
| 2011/0171342 A1* | 7/2011 | Phillips, III | A23G 3/36 426/2 |
| 2013/0287899 A1* | 10/2013 | Rifkin | A23L 29/212 426/72 |
| 2014/0087024 A1 | 3/2014 | Khatib et al. | |

FOREIGN PATENT DOCUMENTS

| | | |
|---|---|---|
| WO | 1999048379 | 9/1999 |
| WO | 2000013522 | 3/2000 |

OTHER PUBLICATIONS https://bodyecology.com/articles/erythritol_what_you_need_to_know_natural_sugar_substitute.php, published Apr. 18, 2008. Retrieved on May 10, 2018. (Year: 2008).*

\* cited by examiner

*Primary Examiner* — Jessica Worsham
(74) *Attorney, Agent, or Firm* — Mohr Intellectual Property Law Solutions, PC

(57) ABSTRACT

In one embodiment, a confectionary comprises 50 to 75 wt. % erythritol, 0 to 75 wt. % of at least one additional sweetener, at least one stabilizer, water, and a first active ingredient. The water may comprise 0.5 to 3 wt. % of the confectionary. The water may have a water activity of from 0.3 to 0.5. The confectionary may be aerated such that the density of the confectionary is 0.05 to 0.3 grams per cubic centimeter.

20 Claims, No Drawings

SHELF-STABLE FOAM-LIKE CONFECTIONARIES COMPRISING ERYTHRITOL AND ACTIVE INGREDIENTS

CROSS REFERENCE TO RELATED APPLICATIONS

This application claims priority to and is a continuation-in-part of copending U.S. application Ser. No. 15/141,055, filed on Apr. 28, 2016, which is hereby incorporated by reference for all purposes. Application Ser. No. 15/141,055 is a continuation-in-part of copending U.S. application Ser. No. 15/068,544, filed on Mar. 12, 2016, which is hereby incorporated by reference for all purposes.

BACKGROUND

The present disclosure relates generally to delivery systems for vitamins, supplements, therapeutic pharmaceutical compounds and other such active ingredients. In particular, edible delivery systems for active ingredients are described. In some embodiments, the edible delivery systems may comprise novel bite-size confectionaries.

Known delivery systems for vitamins and other active ingredients are not entirely satisfactory for the range of applications in which they are employed. For example, some users may have difficulty swallowing conventional active ingredient delivery systems such as pills or capsules. While there are some examples of conventional edible vitamins, these conventional edible vitamins may be difficult and unpleasant to eat, due at least in part to their size and/or dense chalky texture. Furthermore, the texture of "gummy" type vitamins may make them chewy and difficult to eat, while at the same time limiting the amount of active ingredients that can be added.

Thus, there exists a need for edible delivery systems for active ingredients that improve upon and advance the design of known edible delivery systems for active ingredients. Examples of new and useful edible delivery systems for active ingredients relevant to the needs existing in the field are discussed below.

Furthermore, there is an inherent challenge of using traditional food forms as a form of edible delivery system for dietary supplements subject to 21 CFR Part 111, or over-the-counter drugs subject to 21 CFR Part 211, as these regulations require that the traditional food form stay stable and safe for an extended shelf life beyond that of the traditional food form, and that the active ingredients within the traditional food form maintain label claim through the extended shelf life period.

Thus, there exists a need for an edible delivery system for active ingredients that improves upon and advances the shelf life of both the traditional food form and the active ingredients within the traditional food form. Examples of new and useful edible delivery systems for active ingredients, in the form of a dry aerated foam-like confectionary, that improves upon and advances the shelf life of both the confectionary and the active ingredients within the confectionary through the combination of reduced water content and water activity, and in some embodiments, an edible coating, are discussed below.

SUMMARY

In one embodiment, a confectionary comprises 50 to 75 wt. % erythritol, 0 to 75 wt. % of at least one additional sweetener, at least one stabilizer, water, and a first active ingredient. The water may comprise 0.5 to 3 wt. % of the confectionary. The water may have a water activity of from 0.3 to 0.5. The confectionary may be aerated such that the density of the confectionary is 0.05 to 0.3 grams per cubic centimeter.

DETAILED DESCRIPTION

The disclosed edible delivery systems for active ingredients will become better understood through review of the following detailed description. The detailed description provides merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various edible delivery systems for active ingredients are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given FIGURE or example.

In some embodiments, the edible delivery system for active ingredients may take the form of a novel shelf-stable dry aerated foam-like confectionary. The dry aerated foam-like confectionary may be light and crisp with a high fracturability and low bite strength and may dissolve quickly in the mouth, and is distinguishable from creamy, soft and chewy confectionaries such as nougat, marshmallow and gummies. In general, a dry aerated foam-like confectionary in accordance with the present invention comprises erythritol, optionally at least one additional sweetener, at least one stabilizer, water and a first active ingredient. The confectionary may be aerated, thus it may comprises air and/or other inert gas. For example the confectionary may comprise air trapped in small pores or pockets within the confectionary. In some embodiments, the confectionary may be bite sized.

In some embodiments, the aerated dry aerated foam-like confectionary may be a deposited aerated confectionary. In other embodiments, the dry aerated foam-like confectionary may be an extruded aerated confectionary.

In one embodiment, the dry aerated foam-like confectionary may comprise 10 to 85 wt. % sweeteners. Any one (or more than one) of a large number of sweeteners may be used in the confectionary. As used herein, a sweetener is a substance that sweetens. Sweeteners include and sometimes consist of: sugar, sucrose, corn syrup, sorbitol, glucose, fructose, dextrose, agave nectar, stevia, sucralose, SPLENDA, monk fruit, honey, molasses, allulose, erythritol, xylitol, sorbitol, maltitol, polydextrose, aspartame, acesulfame potassium, saccharin, alitame, and tagatose. The aerated confectionary may further comprise coloring and/or flavoring.

In some embodiments, the dry aerated foam-like confectionary may comprise erythritol as the primary sweetener. In these embodiments, the dry aerated foam-like confectionary may comprise 50 to 75 wt. % erythritol, and 0 to 75 wt. % of at least one additional sweetener. In some embodiments the additional sweetener may comprise 0.10 to 0.15 wt. % sucralose. In some embodiments, the additional sweetener may comprise 0.05 to 0.75 wt. % stevia.

The erythritol may function as the main sweetener and/or dry bulking agent. However, the inventors have discovered that in the recited proportions, the erythritol may further function to help set the confectionary and impart an unusually crispy, light and/or quickly dissolving texture.

As described above, a dry aerated foam-like confectionary in accordance with the present invention may comprise one or more stabilizers. The stabilizer may function to help form and retain the pores or pockets of gas within the confectionary. In some embodiments, the dry aerated foam-like confectionary may comprise not greater than 10 wt. % stabilizers. As used herein, a "stabilizer" means an edible material that functions to form pockets or pores in an aerated confectionary. Stabilizers include and sometimes consist of: gelatin, milk protein, egg albumen, egg white gelatin, casein, and soya.

In some embodiments, gelatin is used as the stabilizer. Gelatin as the stabilizer may result in an aerated confectionary having a light, crispy, and dry foam-like texture that has high fracturability and low bite strength after drying or dehydrating. In other embodiments, the stabilizer may comprise one or more whipping agents, such as modified milk protein, egg albumen, pectin, skimmed milk (in spray or dried form), whey, casein, and soya.

In some embodiments, the egg albumen may be heated prior to being mixed into the confectionary. Heating the egg albumen may cause at least some of the proteins therein to denature. The denatured proteins may create a more stable texture and thus extend the shelf life of the aerated confectionary.

The dry aerated foam-like confectionary may be aerated via any method, including chemical aeration and/or mechanical aeration. Methods of mechanical aeration in accordance with the present invention include mixing via a planetary beater, batch pressure beater or continuous pressure beater and/or aeration via a pulling machine.

In some embodiments, the dry aerated foam-like confectionary may be aerated in a pressurized chamber. In these embodiments, the density of the aerated confectionary may be controlled via controlling the duration and/or pressure of the pressurized chamber aeration. Higher pressure may result in smaller, more uniform formation of bubbles within the aerated confectionary. For example, in some embodiments, pressurized chamber aeration at approximately 60 psig may result in small bubbles and thus lead to a relatively firm and dense aerated confectionary. Conversely, lower pressure may result in larger, less uniform formation of bubbles within the aerated confectionary. In some embodiments, the dry aerated foam-like confectionary may be extruded after the pressurized chamber aeration step.

Due at least in part to the aeration, the dry aerated foam-like confectionary may have a relatively low density. For example, in one embodiment, the dry aerated foam-like confectionary may have density of 0.05 to 0.75 grams per cubic centimeter. In other embodiments, the dry aerated foam-like confectionary may have a density of not greater than 0.70 grams per cubic centimeter. In other embodiments, the dry aerated foam-like confectionary may have a density of not greater than 0.65 grams per cubic centimeter. In other embodiments, the dry aerated foam-like confectionary may have a density of not greater than 0.60 grams per cubic centimeter. In other embodiments, the dry aerated foam-like confectionary may have a density of 0.05 to 0.3 grams per cubic centimeter.

Due at least in part to the high erythritol content, the dry aerated foam-like confectionary does not have a melting point. The high-erythritol content confectionaries described herein have a scorch point of 120 degrees Fahrenheit to 130 degrees Fahrenheit. As used herein "scorch point" means the point at which the confectionary begins to burn. In this regard, in some embodiments the dry aerated foam-like confectionary may have a scorch point of at least 120 degrees Fahrenheit. In other embodiments, the dry aerated foam-like confectionary may have a scorch point of at least 125 degrees Fahrenheit. In other embodiments, the dry aerated foam-like confectionary may have a scorch point of at least 130 degrees Fahrenheit. Thus, in some embodiments, the disclosed confectionaries may not need to refrigerated during transport and/or storage.

As described above, a dry aerated foam-like confectionary in accordance with the present invention comprises water. In some embodiments, the water-related properties of the dry aerated foam-like confectionary may be critical to the long shelf-life of the confectionary and the active ingredients contained therein. Specifically, the water content and especially the water activity of the dry aerated foam-like confectionary may, at least in part, control the shelf life of the confectionary and the active ingredients contained therein. In some embodiments, lower water activity may extend the shelf life of the dry aerated foam-like confectionary and the active ingredients contained therein. Similarly, low water content may extend the shelf life of the dry aerated foam-like confectionary and the active ingredients contained therein.

As used herein, water content means the portion of the dry aerated foam-like confectionary that is water, as measured by weight percent (wt. %). As used herein, water activity means the ratio of the vapor pressure of water in a dry aerated foam-like confectionary to the vapor pressure of pure water at the same temperature.

In some embodiment, the dry aerated foam-like confectionary may be at least partially dehydrated. In these embodiments, the dry aerated foam-like confectionary may comprise not greater than 3 wt. % water. In some embodiments, the dry aerated foam-like confectionary may comprise not greater than 2 wt. % water. In some embodiments, the dry aerated foam-like confectionary may comprise not greater than 1 wt. % water. In some embodiments, the dry aerated foam-like confectionary may comprise 0.5 to 3 wt. % water. In some embodiments, the dry aerated foam-like confectionary may comprise 0.5 to 2 wt. % water. In some embodiments, the dry aerated foam-like confectionary may comprise 0.5 to 1 wt. % water. In some embodiments, the dry aerated foam-like confectionary may comprise 0.5 to 0.5 wt. % water.

Methods of dehydrating or drying the dry aerated foam-like confectionary include oven drying, air drying, tray drying, tunnel drying, processing in a dehydrator, microwaving, vacuum drying, freeze drying, processing in a vacuum sealer and/or processing in an oxygen absorber.

In some embodiments, the water of the dry aerated foam-like confectionary may have a water activity of 0.30 to 0.50. In other embodiments, the water of the dry aerated foam-like confectionary may have a water activity of not greater than 0.45. In other embodiments, the water of the dry aerated foam-like confectionary may have a water activity of not greater than 0.40. In other embodiments, the water of the dry aerated foam-like confectionary may have a water activity of not greater than 0.35.

The combination of low water content and low water activity functions to help prevent the degradation of both the active ingredients and the food ingredients within the confectionary. Thus, the shelf life of the food ingredients, active ingredients and confectionary itself, which may fall under the regulations of 21 CFR Part 111. While the low moisture content may, in some embodiments, slow the growth of bacteria, the inventors have discovered that the low moisture content and low water activity may prevent degradation of active ingredients in the absence of bacteria, such as in hermetically sealed containers. As described above, a dry aerated foam-like confectionary in accordance with the present invention comprises at least one active ingredient. As used herein, "active ingredient" means a dietary supplement or pharmaceutical compound. A pharmaceutical compound may be an over-the-counter drug or a prescription drug.

As used herein, "dietary supplement" means a substance intended to add further nutritional value to the diet and not considered food. A "dietary supplement" may be one, or a combination, of the following substances: a vitamin, a mineral, an herb and/or other botanical, an amino acid and/or protein, a fatty acid, an antioxidant, soluble and/or insoluble fiber, a digestive enzyme, a probiotic, a prebiotic, a micronutrient, a macronutrient, a metabolite, an extract, or any other supplements digested to promote the health and well-being of a person.

As used herein, "vitamin" includes and sometimes consists of: Vitamin A, B1 (Thiamine), B2 (Riboflavin), B3 (Niacin), B5 (Pantothenic Acid), B6, B7 (Biotin), B9 (Folic Acid), B12, Choline, C, D, E, K, Bioflavonoids, Coenzyme Q10, Inositol, and PABA (Para-Aminobenzoic Acid), and the like, in liquid or powder form.

As used herein, "Mineral" includes, and sometimes consists of: Calcium, Chromium, Copper, Iodine, Iron, Magnesium, Manganese, Molybdenum, Phosphorus, Potassium, Selenium, Zinc, and the like, in liquid or powder form.

As used herein "fatty acid" includes, and sometimes consists of: Omega 3 ALA (Alpha Linolenic Acid), EPA (Eicosapentaenoic Acid), and DHA (Docosahexaeonic Acid)

As used herein, "dietary supplement" includes, and sometimes consists of one or more of the following: Acai Berry Extract, Aloe Powder, Althea Root (Marshmallow), Apple Fiber Powder, Astragalus Root, Barley Grass, Bee Pollen Powder, Beta Carotene, Betatene, Billberry Extract, Bing Cherry Powder, Biofirm, Black Cohosh, Black Currant Extract, Blackberry Powder, Blueberry Powder, Boron (Boron Citrate), Broccoli Powder, Bromelain, Burdock Root, Cabbage Powder, Caffeine (Caffeine Anhydrous), Calcium (Calcium Ascorbate), Calcium (Calcium Carbonate), Calcium (Calcium Gluconate), Calcium (Calcium Lactate), Calcium (Calcium Silicate), Calcium Citrate, Carrot Powder, Cauliflower Powder, Chamomile Extract, Chlorella, Choline (Choline Bitartrate), Choline (Choline Chloride), Chondroitin Sulfate, Chromium (Chromium Chelate), Chromium (Chromium Picolinate), Cinnamon Bark, Citrus Bioflavanoid, Coconut Oil (deoderized), Coffeeberry Powder, Collagen Peptides, Copper Chelate, CoQ10, Cranberry Powder, Echinacea Power, Elderberry Powder, Fiber (Fibersol), Fiber (Frutalose), Fiber (Polydextrose), Fiber (Raftilose), Flaxseed, GABA, Gamma Oryzanol, Ginkgo Biloba Powder, Ginseng (Korean Red Ginseng), Glucaosmine (Glucosamine HCl), Glucosamine Sulfate, Grape Seed Extract, Guarana Extract, I-Cysteine, IGlutamine, I-Glycine, I-Isoleucine, I-Leucine, I-Lycine, I-Methionine, Inosine, Inositol (Inositol Nicotinate), Iodine (Potassium Iodide), Iron, I-Taurine, I-Tyrosine, I-Valine, Kale Powder, Kelp Powder, Kola Nut, L-Carnitine, Lemon Balm Extract, Lemon Grass Powder, L-Glutamine, LLysine, L-Taurine, L-Theanine, L-Tyrosine, Lutein, Lutein (Floraglo), Lycopene (Lyconat), Lycopene (Redivivo), Magnesium (Gluconal Magnesium), Magnesium (Magnesium Aspartate), Magnesium (Magnesium Citrate), Maitake Powder, Manganese (Manganese Amino Acid Chelate), Manganese (Manganese Sulfate), Mango Powder, Mangosteen Extract, Mate Extract, Melatonin, Molybdenum (Molbdenum Citrate), N-Acetyl-L-Cysteine, Natural Egg Shell Membrane, Nickel (Nickel Amino Acid Chelate), Oat Straw Extract, Orange Crystals, Papain, Papaya Powder, Passion Flower Extract, Peptan, Phaseolamin, Phytosterols (Emulsified), Pineapple Powder, Pomegranate Powder, Potassium (Potassium Ascorbate), Potassium (Potassium Iodide), Probiotic Powder, Prune Powder, Psyllium Seed Husks, Rosehips, Salt, Sea Buckthorn Powder, Selenium (Amino Acid Chelate), Selenium (Sodium Selenate), Shephards Purse, Slippery Elm Bark, Spinach Powder, Spirulina Powder, Strawberry Powder, Sweet Apple Powder, Tomato Powder, Vanadium (Vanadium Citrate), Vitaberry Powder, Vitamin A Palmitate (Retinol), Vitamin B1 (Thiamin Mononitrate), Vitamin B1 Encapsulated (Thiamin), Vitamin B12 (Cobalamin), Vitamin B2 (Riboflavin), Vitamin B2 Encapsulated (Riboflavin), Vitamin B3 (Niacin), Vitamin B3 (Niacinamide), Vitamin B5 (Calcium Pantothenate), Vitamin B6 (Pyridoxal Phosphate), Vitamin B6 Encapsulated (Pyrodoxil Phosphate), Vitamin B7 (Biotin), Vitamin B9 (Folic Acid), Vitamin C (Ascorbic Acid), Vitamin C (Calcium Ascorbate), Vitamin C (Potassium Ascorbate), Vitamin C (Sodium Ascorbate), Vitamin D3 (Ergocalciferol), Vitamin E (Novatol), Vitamin E Acetate (Alpha Tocopherol), Vitamin K1, Wellberry Fruit Extract, Wheat Grass Powder, White Willow, Wild Yam Root Powder, Xylitol, Zinc (Zinc Citrate Dihydrate), Zinc (Zinc Gluconate), Zinc Sulfate, Ω-3 Oil (Algae), Ω-3 Oil (Chia Seed), Ω-3 Oil (Fish), Ω-3 Oil (Flaxseed), Ω-3 Powder (Fish).

As used herein, "pharmaceutical compound" or "drug" means any drug, hormone, peptide, nucleotide, antibody, or other chemical or biological substances used in treatment and prevention of diseases or illness, or substances which affect the structure or function of the body.

As used herein, "pharmaceutical compound" means a prescription or over the counter drug." Pharmaceutical compounds include, and sometimes consist of: an opioid analgesic agent (e.g., as morphine, hydromorphone, oxymorphone, levophanol, methadone, meperidine, fentanyl, codeine, hydrocodone, oxycodone, propoxyphene, buprenorphine, butorphanol, pentazocine and nalbuphine); a non-opioid analgesic agent (e.g., acetylsalicylic acid, acetaminophen, ibuprofen, ketoprofen, indomethacin, diflunisol, naproxen, ketorolac, dichlophenac, tolmetin, sulindac, phenacetin, piroxicam, and mefamanic acid); an anti-inflammatory agent (e.g., glucocorticoids such as alclometas one, fluocinonide, methylprednisolone, triamcinolone and dexamethasone; and nonsteroidal anti-inflammatory drugs such as celecoxib, deracoxib, ketoprofen, lumiracoxib, meloxicam, parecoxib, rofecoxib, and valdecoxib); an antitussive agent (e.g., dextromethorphan, codeine, hydrocodone, caramiphen, carbetapentane, and dextromethorphan); an antipyretic agent (e.g., acetylsalicylic acid and acetaminophen); an antibiotic agent (e.g., aminoglycosides such as, amikacin, gentamicin, kanamycin, neomycin, netilmicin, streptorycin, and tobramycin; carbecephem such as loracarbef; carbapenems such as certapenem, imipenem, and meropenem; cephalosporins such as cefadroxil cefazolin, cephalexin, cefaclor, cefamandole, cephalexin, cefoxitin, cetprozil, cefuroxime, cefftazidine, cefdinir, cefditoren, cetoperazone, cefotaxime, cetpodoxime, ceftazidime, ceftibuten, ceftizoxime, and ceftriaxone; macrolides such as azithromycin, clarithromycin, dirithromycin, erythromycin and troleandomycin; monobactam, penicillins such as amoxicillin, ampicillin, carbenicillin, cloxacillin, dicioxacillin, nafilcillin, oxacillin, penicilin G, penicillin V, piperacillin, and ticarcillin; polypeptides such as bacitracin colstin, and polymycin B; quinolones such as ciprofloxacin, enoxacin, gatifloxacin, levofloxacin, ometloxacin, moxfolxacin, norfloxacin, ofloxacin and trovatioxacin, sulfonamides such as mafenide sulfacetamide, sulfamethizole, sulfasalazine, sulfisoxazole, and trimethoprim-sulfamethoxazole; and tetracyclines such as demeclocycline, doxycycline, minocycine, and oxytetracycline); an antimicrobial agent (e.g., ketoconazole, amoxicillin, cephalexin, miconazole, econazole, acyclovir, and nelfinavir); a steroidal agent (e.g., estradiol, testosterone, cortisol, aldosterone, prednisone, and cortisone); an amphetamine stimulant agent (e.g., amphetamine); a non-amphetamine stimulant agent (e.g., methylphenidate, nicotine, and caffeine); a laxative agent (e.g., bisacodyl, casanthranol, senna, and castor oil); an anorexic agent (e.g., fenfluramine, dexfenfluramine, mazindol, phentermine, and aminorex); an antihistaminic agent (e.g., phencarol, cetirizine, cinnarizine, ethamidindole, azatadine, brompheniramine, hydroxyzine, and chlorpheniramine); an antiasthmatic agent (e.g., zileuton, montelukast, omalizumab, fluticasone, and zafirlukast); an antidiuretic agent (e.g., desmopressin, vasopressin, and lypressin); an antiflatulant agent (e.g., simethicone); an antimigraine agent (e.g., naratriptan, frovatriptan, eletriptan, dihydroergotamine, zolmitriptan, almotriptan, and sumatriptan); an antispasmodic agent (e.g., dicyclomine, hyoscyamine, and peppermint oil); an antidiabetic agent (e.g., methformin, acarbose, miglitol, pioglitazone, rosiglitazone, troglitazone, nateglinide, repaglinide, mitiglinide, saxagliptin, sitagliptine, vildagliptin, acetohexamide, chlorpropamide, gliclazide, glimepiride, glipizide, glyburide, tolazamide, and tolbutamide); an antacid (e.g., aluminium hydroxide, magnesium hydroxide, calcium carbonate, sodium bicarbonate, and bismuth subsalicylate); a respiratory agent (e.g., albuterol, ephedrine, metaproterenol, and terbutaline); a sympathomimetic agent (e.g., pseudoephedrine, phenylephrine, phenylpropanolamine, epinephrine, norepinephrine, dopamine, and ephedrine); an H2 blocking agent (e.g., cimetidine, famotidine, nizatidine, and ranitidine); an antihyperlipidemic agent (e.g., clofibrate, cholestyramine, colestipol, fluvastatin, atorvastatin, genfibrozil, lovastatin, niacin, pravastatin, fenofibrate, colesevelam, and simvastatin); an antihypercholesterol agent (e.g., lovastatin, simvastatin, pravastatin, fluvastatin, atorvastatin, cholestyramine, colestipol, colesevelam, nicotinic acid, gemfibrozil, and ezetimibe); a cardiotonic agent (e.g., digitalis, ubidecarenone, and dopamine); a vasodilating agent (e.g., nitroglycerin, captopril, dihydralazine, diltiazem, and isosorbide dinitrate); a vasocontricting agent (e.g., dihydroergotoxine and dihydroergotamine); a sedative agent (e.g., amobarbital, pentobarbital, secobarbital, clomethiazole, diphenhydramine hydrochloride, and alprazolam); a hypnotic agent (e.g., zaleplon, zolpidem, eszopiclone, zopiclone, chloral hydrate, and clomethiazole); an anticonvulsant agent (e.g., lamitrogene, oxycarbamezine, pheytoin, mephenytoin, ethosuximide, methsuccimide, carbamazepine, valproic acid, gabapentin, topiramate, felbamate, and phenobarbital); a muscle relaxing agent (e.g., baclofen, carisoprodol, chlorzoxazone, cyclobenzaprine, dantrolene sodium, metaxalone, orphenadrine, pancuronium bromide, and tizanidine); an antipsychotic agent (e.g., phenothiazine, chlorpromazine, fluphenazine, perphenazine, prochlorperazine, thioridazine, trifluoperazine, haloperidol, droperidol, pimozide, clozapine, olanzapine, risperidone, quetiapine, ziprasidone, melperone, and paliperidone); an antianxiolitic agent (e.g., lorazepam, alprazolam, clonazepam, diazepam, buspirone, meprobamate, and flunitrazepam); an antihyperactive agent (e.g., methylphenidate, amphetamine, and dextroamphetamine); an antihypertensive agent (e.g., alphamethyldopa, chlortalidone, reserpine, syrosingopine, rescinnamine, prazosin, phentolamine, felodipine, propanolol, pindolol, labetalol, clonidine, captopril, enalapril, and lisonopril); an anti-neoplasia agent (e.g., taxol, actinomycin, bleomycin A2, mitomycin C, daunorubicin, doxorubicin, epirubicin, idarubicin, and mitoxantrone); a soporific agent (e.g., zolpidem tartrate, eszopiclone, ramelteon, and zaleplon); a tranquilizer (e.g., alprazolam, clonazepam, diazepam, flunitrazepam, lorazepam, triazolam, chlorpromazine, fluphenazine, haloperidol, loxapine succinate, perphenazine, prochlorperazine, thiothixene, and trifluoperazine); a decongestant (e.g., ephedrine, phenylephrine, naphazoline, and tetrahydrozoline); a beta blocker (e.g., levobunolol, pindolol, timolol maleate, bisoprolol, carvedilol, and butoxamine); an alpha blocker (e.g., doxazosin, prazosin, phenoxybenzamine, phentolamine, tamsulosin, alfuzosin, and terazosin); a non-steroidal hormone (e.g., corticotropin, vasopressin, oxytocin, insulin, oxendolone, thyroid hormone, and adrenal hormone); a herbal agent (e.g., glycyrrhiza, aloe, garlic, nigella sativa, rauwolfia, St John's wort, and valerian); an enzyme (e.g., lipase, protease, amylase, lactase, lysozyme, and urokinase); a humoral agent (e.g., prostaglandins, natural and synthetic, for example, PGE1, PGE2alpha, and PGF2alpha, and the PGE1 analog misoprostol); a psychic energizer (e.g., 3-(2-aminopropy)indole and 3-(2-aminobutyl)indole); a vitamin (e.g., retinol, retinal, retinoic acid, 3-dehydroretinol, thiamine, riboflavin, niacin, pantothenic acid, pyridoxine, biotin, folic acid, cyanocobalamin, ascorbic acid, lumisterol, ergocalciferol, cholecalciferol, dihydrotachysterol, tocopherol, and naphthoquinone); a mineral (e.g., calcium, iron, zinc, selenium, copper, iodine, magnesium, phosphorus, and chromium); an anti-nausea agent (e.g., dolasetron, granisetron, ondansetron, tropisetron, meclizine, and cyclizine); a hematinic agent (e.g., ferrous salts, ferrous amino chelates, ferrous sulfate, ferrous fumarate, Ferrochel iron); a nutritional product (e.g., bee pollen, bran, wheat germ, kelp, cod liver oil, ginseng, and fish oils, amino acids, proteins, and mixtures thereof); and a fiber product (e.g., stabilizing, lignin, polydextrose, prebiotics, waxes, chitins, pectins, beta-glucans, inulin, and oligosaccharides.

OTCs may include any of the following brand name or generic equivalent drugs: BENADRYL®, SUDAFED®, CLARITIN®, MAALOX®, MYLANTA®, INSULIN, TUMS®, PEPCID® AC, MONISTAT®, EX-LAX®, IMODIUM® A.D., ROBITUSSIN®, CHLORASEPTIC®, THERA-FLU®, ALKA-SELTZER, MOTRIN®, DRAMAMINE®, and the like, in liquid or powder form.

A pharmaceutical compound may include a prescription drug. Such prescription drugs such may include brand name or generic forms of LIPITOR®, SINGULAIR®, LEXAPRO, PLAVIX®, MORPHINE, HYDROCODONE (VICODIN®), DEMEROL®, CODEINE, DIAZEPAM (VALIUM®), PENICILLIN, PREVACID®, ALLEGRA-D®, CELEBREX®, CRESTOR®, CIALIS®, VALTREX®, VIAGRA®, CIALIS®, PRILOSEC®, LIPITOR®, AMBIEN CR®, VIAGRA®, FLOMAX®, PROZAC®, and the like, in liquid or powder form. In some embodiments, in addition to an active pharmaceutical ingredient, the active ingredients of the delivery system may also include a combination of dietary supplements. The inclusion of dietary supplements with pharmaceutical compounds will depend in part on the compatibility of the supplement with the pharmaceutical compound.

In one embodiment, the dry aerated foam-like confectionary may comprise an edible coating. The edible coating may fully envelop a dry aerated foam-like confectionary piece. In some embodiments, the edible coating may help to maintain optimal moisture content and/or water activity within the dry aerated foam-like confectionary piece. The edible coating may further function to limit the confectionary's exposure to light and air. Thus, the edible coating may aid in extending the shelf life of the confectionary beyond that of a conventional confectionary. In some embodiments, the edible coating may be porous, and in some embodiments, the edible coating may be non-porous, for example the edible coating may comprise a hard candy shell or a chocolate or yogurt coating.

In some embodiments, the edible coating comprises at least one sweetener and water. The moisture content of the edible coating may determine, at least in part, the ability of the edible coating to maintain optimal moisture content and/or water activity within the aerated confectionary center. The edible coating may further comprise coloring and or flavoring. In some embodiments, the edible coating may comprise one or more of the above described active ingredients. In some embodiments, an edible coating containing active ingredients may allow the confectionary as a while to contain a higher amount of active ingredients than would be possible if the active ingredients were solely in the confectionary itself.

In one embodiment, the edible coating comprises 0.1 to 6 wt. % water. In other embodiments, the edible coating comprises 0.1 to 4 wt. % water. In other embodiments, the edible coating comprises 0.1 to 3 wt. % water. In other embodiments, the edible coating comprises 0.1 to 2 wt. % water. In other embodiments, the edible coating comprises 0.1 to 1 wt. % water.

In some embodiments, the dry aerated foam-like confectionary comprises at least one void formed within the confectionary and a filling placed in the void. In some embodiments, the void may be made mechanically, for example, via a press. In some embodiments, the void may be made via air pressure. The filling may comprise a sweetener, flavorings, and at least one of the above described active ingredients. In some embodiments, the void formed within the confectionary may help the confectionary to set properly when active ingredients with high acidity, such as Vitamin C, are placed directly and solely in the void rather than in the confectionary itself. In some embodiments, filling the void formed within the confectionery with active ingredients may allow the confectionary as a whole to contain a higher amount of active ingredients than would be possible if the active ingredients were solely in the confectionary itself. In some embodiments, filling the void formed within the confectionary with active ingredients may allow for greater precision in the amount of active ingredients placed in the confectionary.

In one embodiment, the dry aerated foam-like confectionary may be injected with a pectin gel. The pectin gel may contain a desiccant, such as a silica desiccant. The desiccant may serve to maintain optimal moisture levels within the aerated confectionary.

EXAMPLE 1—SHELF-STABLE FORTIFIED AERATED FOAM-LIKE CONFECTIONARY

A shelf-stable and vitamin-fortified dry aerated foam-like confectionary mixture was prepared as follows. Gelatin was allowed to bloom in a first amount of water. Egg white powder was added to a second amount of water in a 1:2 ratio, and then agitated to until soft peaks formed. Cream of tartar, salt, and sucralose were slowly added to the egg white/water mixture, then agitated under high agitation to maintain soft peaks of the egg white/water mixture. Erythritol was slowly added to the egg white/water mixture. The egg white/water mixture was then agitated under high agitation until stiff peaks formed. Concurrently, hot water was added to the gelatin/water mixture, and heated. The gelatin/water mixture was then slowly added to the egg white/water mixture, and agitated. The final ingredients comprising flavorings and active ingredients were slowly added to the resulting mixture during agitation. The resulting mixture was agitated under high agitation in a room temperature bowl for 4-6 minutes. The resulting aerated confectionary mixture was deposited into 1 to 2 gram pieces, allowed to air dry for 24 to 36 hours, and enrobed in a chocolate compound coating to extend shelf life.

EXAMPLE 2—SHELF-STABLE ENROBED MULTIVITAMIN FORTIFIED DRY AERATED FOAM-LIKE CONFECTIONARY

A dry aerated foam-like confectionary mixture was prepared in accordance with Example 1 using 14 grams of powdered egg whites, 0.14 grams of sucralose as the masking sweetener, 2.8 grams of cream of tartar, 6.5 grams of flavoring, 1.7 grams of food coloring, 296 grams of water, 112 grams of erythritol as the bulking sweetener, 14 grams of gelatin as a stabilizer, and 32 grams of multivitamin blend as the active ingredients. The resulting aerated confectionary mixture was then deposited in 1 to 2 g drops on a silicon mat, and each piece was dried completely then enrobed in a red vanilla compound coating to extend self-life and durability.

EXAMPLE 3—SHELF-STABLE ENROBED VITAMIN C FORTIFIED DRY AERATED FOAM-LIKE CONFECTIONARY

A dry aerated foam-like confectionary mixture was prepared in accordance with Example 1 using 14 grams of powdered egg whites, 0.14 grams of sucralose as the masking sweetener, 2.8 grams of cream of tartar, 6.5 grams of flavoring, 1.7 grams of food coloring, 296 grams of water, 112 grams of erythritol as the bulking sweetener, and 14 grams of gelatin as a stabilizer. The resulting aerated confectionary mixture was then deposited in 1 to 2 gram drops on a silicon mat and dried completely. Depressions were made in each individual confectionery pieces using mechanical means, and a mixture of 100 mg Vitamin C as the active ingredient and 50 mg of Sugar as a sweetener were deposited into the depressions. The resulting aerated confectionery mixture was then deposited in 1 to g drops on a silicone mat, and each piece was dried completely, and then enrobed in a milk chocolate compound coating to extend self-life and durability.

EXAMPLE 4—SHELF-STABLE VITAMIN B COMPLEX FORTIFIED DRY AERATED FOAM-LIKE CONFECTIONARY

A dry aerated foam-like confectionary mixture was prepared in accordance with Example 1 using 14 grams of powdered egg whites, 0.14 grams of sucralose as the masking sweetener, 2.8 grams of cream of tartar, 6.5 grams of flavoring, 1.7 grams of food coloring, 296 grams of water, 112 grams of erythritol as the bulking sweetener, 14 grams of gelatin as a stabilizer, and 9 grams of B-complex vitamin blend as the active ingredients. The resulting aerated confectionary mixture was then deposited in 1 to 2 g drops on a silicon mat, and each piece was dried completely, and then enrobed in a chocolate compound coating to extend shelf life.

EXAMPLE 5—DRY AERATED FOAM-LIKE CONFECTIONARY WITH ERYTHRITOL COMPARED TO ERYTHRITOL-FREE CONFECTIONARIES

Mixtures were prepared with egg white powder, gelatin, cream of tartar, sucralose (minute quantity), erythritol, flavoring, coloring, water, and various active ingredients. The mixtures were aerated using a planetary mixer on high speed until room temperature and stiff, but able to be piped through a pastry bag. The mixtures were deposited in 1 to 2 gram drops on a silicon mat and left to dry at room temperature overnight or for several days.

Comparison aerated foam confectionaries were prepared in a manner similar to that described above, but with the erythritol substituted for other bulking sweeteners.

The aerated foam-like confectionaries containing erythritol set successfully. These erythritol-containing products were found to have a unique crunchy texture and may be characterized as quickly dissolving on the tongue. The unusual crunchy texture was also found to persist for an extended shelf-life. Conversely, the erythritol-free comparison confectionaries were found to have a soft, sticky and chewey texture, especially when placed in the mouth. Furthermore, the erythritol-free comparison confectionaries were found to soften undesirably over time.

Thus, the erythritol appears to have a combined effect on texture and setting. Without wishing to be bound by theory, it is believed that the relatively low hygroscopic properties of erythritol relative to the other sweeteners may play a role in creating the unique crunchy texture and extended shelf-life of the aerated foam confectionaries containing erythritol.

While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A confectionary, comprising:
50 to 75 wt. % erythritol;
   wherein the erythritol is dissolved in the confectionary;
   wherein the erythritol imparts a crunchy texture to the confectionary;
0 to 75 wt. % of at least one additional sweetener;
at least one stabilizer;
water;
   wherein the water comprises 0.5 to 3 wt. % of the confectionary;
   wherein the water has a water activity of 0.3 to 0.5; and
a first active ingredient;
wherein the confectionary is aerated such that the density of the confectionary is 0.05 to 0.3 grams per cubic centimeter.

2. The confectionary of claim 1, wherein the confectionary has a scorch point of at least 120 degrees Fahrenheit.

3. The confectionary of claim 1, wherein the confectionary has a melting point of at least 120 degrees Fahrenheit.

4. The confectionary of claim 1, wherein the at least one stabilizer is selected from the group consisting of: gelatin, milk protein, egg albumen, egg white gelatin, casein, and soya.

5. The confectionary of claim 1, wherein the water comprises not greater than 2 wt. % of the confectionary.

6. The confectionary of claim 1, wherein the water activity is not greater than 0.45.

7. The confectionary of claim 1, wherein the first active ingredient is selected from the group consisting of: dietary supplements and pharmaceutical compounds.

8. The confectionary of claim 7, wherein the first active ingredient is a dietary supplement selected from the group consisting of: a vitamin, a mineral, an herb and/or other botanical, an amino acid and/or protein, a fatty acid, an antioxidant, a soluble and/or insoluble fiber, a digestive enzyme, a probiotic, a prebiotic, a micronutrient, a macronutrient, a metabolite, and an extract.

9. The confectionary of claim 7, wherein the first active ingredient is a pharmaceutical compound selected from the group consisting of: an opioid analgesic agent; a non-opioid analgesic agent; an anti-inflammatory agent; an antitussive agent; an antipyretic agent; an antibiotic agent; an antimicrobial agent; a steroidal agent; an amphetamine stimulant agent; a non-amphetamine stimulant agent; a laxative agent; an anorexic agent; an antihistaminic agent; an antiasthmatic; an antidiuretic agent; an antiflatulant agent; an antimigraine agent; an antispasmodic agent; an antidiabetic, an antacid; a respiratory agent; a sympathomimetic agent; an H2 blocking agent; an antihyperlipidemic agent; an antihypercholesterol agent; a cardiotonic agent; a vasodilating agent; a vasoconstricting agent; a sedative agent; a hypnotic agent; an anticonvulsant agent; a muscle relaxing agent; an antipsychotic agent; an antianxiolitic agent; an antihyperactive agent; an antihypertensive agent; an anti-neoplasia agent; a soporific agent; a tranquilizer; a decongestant; a beta blocker; an alpha blocker; a non-steroidal hormone; a herbal agent; an enzyme; a humoral agent; a psychic energizer; a vitamin; a mineral; an anti-nausea agent; a hematinic agent; a nutritional product; and a fiber product.

10. The confectionary of claim 1, further comprising an edible coating.

11. The confectionary of claim 10, wherein the edible coating is nonporous.

12. The confectionary of claim 11, wherein the edible coating comprises a sweetener and water.

13. The confectionary of claim 12, wherein the water of the edible coating comprises 0.1 to 6 wt. % of the edible coating.

14. The confectionary of claim 12, wherein the water of the edible coating comprises 0.1 to 2 wt. % of the edible coating.

15. The confectionary of claim 12, wherein the water of the edible coating comprises 0.1 to 1 wt. % of the edible coating.

16. The confectionary of claim 12 wherein the water of the edible coating has a water activity of 0.35 to 0.75.

17. The confectionary of claim 10, wherein the edible coating comprises a second active ingredient selected from the group consisting of: dietary supplements, over-the-counter drugs, prescription drugs, and pharmaceutical compounds.

18. The confectionary of claim 17, wherein the second active ingredient is a dietary supplement selected from the group consisting of: a vitamin, a mineral, an herb and/or other botanical, an amino acid and/or protein, a fatty acid, an antioxidant, soluble and/or insoluble fiber, a digestive enzyme, a probiotic, a prebiotic, a micronutrient, a macronutrient, a metabolite, and an extract.

19. The confectionary of claim 17, wherein the second active ingredient is a pharmaceutical compound selected from the group consisting of: an opioid analgesic agent; a non-opioid analgesic agent; an anti-inflammatory agent; an antitussive agent; an antipyretic agent; an antibiotic agent; an antimicrobial agent; a steroidal agent; an amphetamine stimulant agent; a non-amphetamine stimulant agent; a laxative agent; an anorexic agent; an antihistaminic agent; an antiasthmatic; an antidiuretic agent; an antiflatulant agent; an antimigraine agent; an antispasmodic agent; an antidiabetic, an antacid; a respiratory agent; a sympathomimetic agent; an H2 blocking agent; an antihyperlipidemic agent; an antihypercholesterol agent; a cardiotonic agent; a vasodilating agent; a vasocontricting agent; a sedative agent; a hypnotic agent; an anticonvulsant agent; a muscle relaxing agent; an antipsychotic agent; an antianxiolitic agent; an antihyperactive agent; an antihypertensive agent; an antineoplasia agent; a soporific agent; a tranquilizer; a decongestant; a beta blocker; an alpha blocker; a non-steroidal hormone; a herbal agent; an enzyme; a humoral agent; a psychic energizer; a vitamin; a mineral; an anti-nausea agent; a hematinic agent; a nutritional product; and a fiber product.

20. The confectionary of claim 17 comprising:
a void formed within the confectionary; and
a filling disposed in the void, wherein the filling comprises a sweetener and a third active ingredient.

* * * * *